United States Patent [19]

Janssen

[11] Patent Number: 5,749,914
[45] Date of Patent: May 12, 1998

[54] CATHETER FOR OBSTRUCTED STENT

[75] Inventor: Michael Janssen, Englewood, Colo.

[73] Assignee: Advanced Coronary Intervention, Englewood, Colo.

[21] Appl. No.: 654,146

[22] Filed: May 28, 1996

Related U.S. Application Data

[60] Continuation-in-part of Ser. No. 531,453, Sep. 21, 1995, Pat. No. 5,626,576, which is a division of Ser. No. 230,439, Apr. 19, 1994, Pat. No. 5,454,809, which is a continuation of Ser. No. 96,651, Jul. 22, 1993, abandoned, which is a continuation of Ser. No. 974,670, Nov. 12, 1992, abandoned, which is a continuation of Ser. No. 849,638, Mar. 5, 1992, abandoned, which is a continuation of Ser. No. 637,992, Jan. 3, 1991, abandoned, which is a continuation of Ser. No. 294,270, Jan. 6, 1989, abandoned.

[51] Int. Cl.$^6$ ....................................................... A61N 1/44
[52] U.S. Cl. .................................................. 607/116; 128/642
[58] Field of Search ......................... 623/1; 128/660.03, 128/642; 606/39–41; 607/122, 116

[56] References Cited

U.S. PATENT DOCUMENTS

| | | | |
|---|---|---|---|
| 4,682,596 | 7/1987 | Boles et al. | 128/303.14 |
| 4,735,205 | 4/1988 | Chachques et al. | 128/785 X |
| 4,832,048 | 5/1989 | Cohen | 128/786 |
| 4,920,980 | 5/1990 | Jackowski | 128/642 |
| 4,979,510 | 12/1990 | Franz et al. | 607/122 X |
| 5,044,375 | 9/1991 | Bach, Jr. et al. | 128/786 |
| 5,078,736 | 1/1992 | Behl | 623/1 |
| 5,263,977 | 11/1993 | Adams et al. | 607/122 |
| 5,345,940 | 9/1994 | Seward et al. | 128/660.03 |
| 5,356,427 | 10/1994 | Miyata et al. | 607/122 |
| 5,511,426 | 4/1996 | Hummel et al. | 607/122 X |
| 5,578,067 | 11/1996 | Ekwall et al. | 607/122 |
| 5,584,872 | 12/1996 | Lafontaine et al. | 128/642 X |

*Primary Examiner*—Francis Jaworski
*Attorney, Agent, or Firm*—Davis, Graham & Stubbs, LLP

[57] ABSTRACT

Obstructive material is removed from a stent by modified electrosurgical ablation. A modified electrosurgical device having at least one electrode is positioned within the stent, and current is supplied to the electrode. The electrode is prevented from physically contacting the stent, such as by being situated within a groove on the device. The stent may, but need not be, grounded to the current source. The device may be properly positioned within the stent by using ultrasound transducers, fiber optics, or other means. Additionally, the device may be positioned by including at least two electrodes, and measuring the impedance therebetween, as the impedance will be relatively low when both electrodes are within a conductive stent. Therapeutic fluid may be supplied through the catheter, and energy may be supplied to increase the activity of the fluid.

41 Claims, 5 Drawing Sheets

CATHETER FOR OBSTRUCTED STENT

CROSS REFERENCE TO RELATED APPLICATIONS

This application is a continuation-in-part of application Ser. No. 08/531,453 filed Sep. 21, 1995 and now U.S. Pat. No. 5626576 which is a divisional application of application Ser. No. 08/230,439 filed Apr. 19, 1994, now issued as U.S. Pat. No. 5,454,809 on Oct. 3, 1995, which is a continuation of application ser. No. 08/096,651 filed Jul. 22, 1993, now abandoned, which is continuation of application Ser. No. 07/974,670 filed Nov. 12, 1992, now abandoned, which is a continuation of application Ser. No. 07/849,638 filed Mar. 5, 1992, now abandoned, which is a continuation of Ser. No. 07/637,992 filed Jan. 3, 1991 now abandoned, which is a continuation of application Ser. No. 07/294,270 filed Jan. 6, 1989, now abandoned.

FIELD OF THE INVENTION

The present invention relates to the field of catheters that remove obstructions from a tubular passageway of a patient, and more particularly to a catheter that uses ablation, such as radio frequency (RF) ablation, to remove obstructions from a tubular passageway that has been implanted with a stent.

BACKGROUND OF THE INVENTION

Various methods have been used to remove obstructions from a tubular passageway (lumen) in the body of a patient. Such obstructions may occur in virtually all of the lumens in a body, and may be composed of many different substances. One example of such an obstruction is atherosclerotic plaque that may form within a coronary artery and may, if left untreated, prove fatal to the patient. However, obstructions may occur in any vein or artery such as a coronary, carotid, neurological, peripheral, or renal vein or artery. Other potentially obstructed lumens include bile ducts, all lumens of the genital-urinary tract such as fallopian tubes, and lumens of the gastrointestinal tract such as the intestines or colon. Examples of obstructive material are all forms of plaque such as fatty plaque, fibrous plaque, and calcific plaque; fibrotic material; mucous; thrombus; and blood clots. These lumens and obstructive materials are given as examples only—many types of obstructions may occur within all of the lumens within the body. Any of these obstructions interfere with material transport and fluid flow within the lumen. In the case of the coronary arteries, such an obstruction may cause heart failure, such as a heart attack, which may prove fatal. Obstructions within other lumens cause a variety of medical problems that may vary depending upon the specific lumen.

It may be medically desirable to treat any of these obstructed lumens. A variety of methods and devices have been developed to remove these obstructions, or to at least alleviate their obstructing effect. For example, balloon angioplasty techniques include introducing a catheter having a deflated balloon into the obstructed lumen to the obstruction site, and inflating the balloon. The inflated balloon presses into the obstruction, or the wall of the lumen if no obstruction is present. Frequently, the balloon will press against both obstruction material and the wall of the lumen, as the obstruction material is not symmetrically located around the circumference of a lumen.

The balloon stretches the lumen, so that the lumen is widened and the fluid flow through the lumen may be improved. However, balloon angioplasty does not remove the obstruction; instead, the balloon normally fractures plaque and stretches the elastic artery beyond its ability to recoil. A major shortcoming of balloon angioplasty is that the same elastic qualities of tissue lumens that allow them to be stretched also often cause the lumens to contract after the balloon is deflated and withdrawn from the lumen. The contracted lumen causes a restricted blood flow, so that the patient is no better off than before the angioplasty was performed, and may in fact be worse. While the angioplasty may be repeated, the operation is not without risks. Besides the risks involved in any surgical procedure, the balloon (or other mechanical) angioplasty involves a risk of rupturing the lumen. If this is a major blood vessel, as is often the case, death may result. Other complications, for example, dissections, flaps, tears, and restenosis, are also common, and may also result in severe injury and death.

A solution to the problem of lumen contraction has been to insert an at least semi-rigid structure, such as a tube, into the lumen. This prevents the lumen from retracting to a smaller diameter than the tube. Such tubes are known as stents. Experimentation with stents has occurred since at least the 1960's. However, they have not come into widespread use until the 1990's.

While the theory behind stents is quite simple and they have proven effective in preventing lumen restriction, complications often may arise in their use. In particular, obstructions may build up in or through the stent in much the same manner as they would if the stent was not in place, such as by, for example, tissue growth. Stents are commonly made so that they may be compressed as they are inserted through the lumen to the obstruction site, and then expanded, such as by, for example, inflating a balloon at the appropriate site. For example, stents are commonly made of wire mesh, although they are made of other materials and in other mechanical configurations. Other stent designs are designed to self expand and may be introduced under tension, or by other means.

This mesh (or other) design gives the stents a mechanical strength that helps to prevent the lumen from constricting the expanded stent. Also, a stent is commonly designed to have a reduced surface area. The stent irritates the tissue at least to some extent and allows for thrombin, plaque, or other substances to accumulate within the interior surface or on the boundary of the stent. Such accumulation may again restrict fluid flow through the lumen, so that efficacy of the stent is reduced or, in severe cases, eliminated. Flow through a stent may also be restricted because of incomplete or otherwise improper deployment of the stent, or for other reasons.

Various devices other than balloon angioplasty have been developed to remove obstructions from tissue lumens. Catheters equipped with cutting blades may be used to slice the obstruction from the lumen. Means for removing the severed obstruction must be completely effective, or the loosened obstruction may lodge in the lumen and completely restrict fluid flow therethrough. Various devices use heat to resolve obstruction material, such as are described in U.S. Pat. Nos. 4,654,024 of Crittendon et al. and 4,748,979 and 4,672,962 of Hershenson. Laser angioplasty devices generally supply energy to the tip of a catheter to cauterize or burn away obstructions. See, for example, U.S. Pat. Nos. 4,784,133 of Mackin; 4,685,458 of Lechrone; 4,770,653 of Shturman; 4,662,368 and 4,773,413 of Hussein; and 4,732,448 and 4,641,912 of Goldenberg.

Radio frequency (RF) ablation is also known in the prior art to ablate obstruction material. In catheters, RF current is directed from an RF power source to an ablating electrode, from which the RF current travels through the obstruction material. In a monopolar device, the current return is generally through a relatively large conductive plate (patient plate) attached to the body of a patient back to the power supply. In a bipolar device, more than one electrode is present at the distal end of the catheter, and the current flows through the obstruction site between at least two of these electrodes. An RF catheter is described in U.S. Pat. No. 5,454,809 of Janssen. The catheter described therein could be used in a lumen containing a stent.

However, the presence of a stent causes some complications for RF ablation. The stent is, in general, formed of conductive material, such as wire mesh. If an ablating electrode came into contact with the stent, a short circuit could occur, which may damage the ablation catheter, the stent, or the lumen. However, the stent may also in some ways allow for improved ablation. One difficulty in all forms of angioplasty is determining the precise location of an angioplasty catheter within the lumen. The present invention allows for the stent to be used to determine the position of an ablating catheter, and for the subsequent ablation of the obstructive material. Another difficultly in ablation is controlling the current. The present invention overcomes these and other difficulties by providing a catheter and a method of use particularly suited to be used within a stent.

Prior art has shown that the application of light may prevent restenosis and may otherwise be useful in internal surgery. Such energy application is described in, for example, U.S. Pat. Nos. 5,053,033 and 5,370,608. However, the application of such energy in connection with a stent, and particularly in the ablation of obstructive material, is unknown in the art.

SUMMARY OF THE INVENTION

The present invention provides a device and a method for removing obstructive material that has formed on or within a stent that has been implanted within a lumen of a subject. The device is a catheter of the type that may be inserted within any of the above discussed lumens. The device may be inserted using a guide wire of any known type, or by other guidance means.

The distal end of the catheter includes means for applying ablative energy to the obstructive material. Such energy may be any electromagnetic energy delivered in any wave form or modulation, mechanical energy such as a direct mechanical force or acoustical or vibrational energy. A particularly effective form of energy is electrical current, such as radio frequency current. A device that uses current as the ablative energy has at least one electrode situated on or proximate to its distal end. The electrode is recessed from the catheter surface, or the catheter surface has spacers extending therefrom, so that the electrode is prevented from making direct physical contact with the stent.

When the device is properly positioned within the stent, current is supplied from the electrode and flows through the obstructive material, thereby ablating and removing the material. Depending on the embodiment of the device, the current may also flow through the stent. This may be done by exploiting the conductive nature of a stent, or by directly grounding the stent with a stylet or probe. Alternatively, the current may be directed so as to be contained substantially within the surface or body of the stent.

A plurality of electrodes may be used. The electrodes may be divided both along the longitudinal and circumferential directions of the catheter. The longitudinal divisions allow for selective, controlled ablation over the length of the stent. The circumferential divisions allow for selectively ablating nonsymmetrical obstructions that have formed around the surface of the stent.

The catheter may include means to visualize the interior of the lumen in which it is inserted. Such means may include ultrasound transducers, fiber optics, or other means. The catheter may be precisely positioned based on the visualization, and, after ablation is partially performed, the catheter may be repositioned for further ablation. Such visualization techniques may also be used to determine the location of the catheter within the lumen within the framework of the stent, the location of the stent, and the composition and configuration of the obstructive material.

Positioning of the catheter may be further aided by sensing the impedance between multiple electrodes on the catheter. The impedance will vary depending on whether the electrodes are within or not within the stent, because the stent is (in general) conductive and provides a change in electrical properties and propagation. For example, a stent may provide a good current path between two electrodes within the stent. By successively sensing impedance between electrodes and moving the catheter, the electrodes may be positioned within the stent before ablating energy is supplied.

The catheter may be designed so that the electrode area is longer than the stent, or may be positioned so that part of the electrode area protrudes beyond the stent. The positioning of the catheter within the stent framework may be determined by selectively applying sensing signals to different electrical sensors. Once catheter positioning is detected, ablation of the obstructive material may be directed. The same electrodes may be used for sensing and ablating, or separate sensing and ablating electrodes may be provided.

The device may also deliver fluid or solution through the catheter, and deliver fluid or solution through or near the distal end. Such fluid may be useful to help ablate the obstructive material, prevent or reduce restenosis, or for other therapeutic or diagnostic purposes. Further, energy may be supplied by the device to increase the efficacy of the fluid. This energy may be electrical energy supplied through the ablating or sensing electrode(s). Or, the energy may be separately supplied, such as optical, mechanical, or acoustical energy.

The energy may be continuous, intermittent, pulsed, modulated, or otherwise controlled so as to produce the maximum desired effect. The fluid or solution may contain suspended materials, chemical, or other therapeutic or diagnostic agents. If electricity is used to enhance the fluid or solution effect, the electricity may be applied to provide electroporation, iontophoresis, electro-osmosis, iontherapy, or other method of using energy to either force, assist, or increase the efficacy of the fluid or solution, or otherwise increase bioabsorption or bioavailability.

The device may also include means such as electrodes to ablate obstructive material that is not within a stent. Electrodes used within a stent will normally be situated so that they do not contact the stent, else a short circuit may result. Conversely, electrodes may be intentionally designed to contact the stent so as to direct current flows, apply therapeutic energy, or otherwise produce a desired effect such as removing obstructive material or reducing or discouraging regrowth or deposition of the same. In either event, the electrodes to ablate obstructive material out of a stent should be positionable against or very close to the obstructive material. Therefore, one embodiment of the invention includes two sets of electrodes. The first set is recessed and is used to ablate within the stent; the second set is extended and used to ablate at either end of the stent.

DETAILED DESCRIPTION OF THE INVENTION

Figure 1:
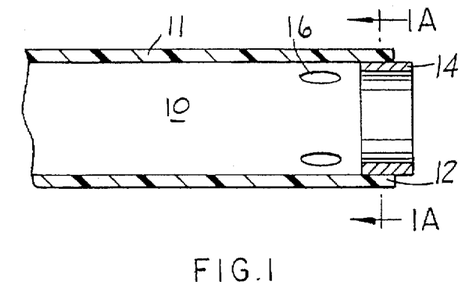
FIG. 1 is a longitudinal cross section of the distal end of an embodiment of the invention, showing an electrode disposed within an elongate tube.

FIG. 1 shows a longitudinal cross section of the distal end 10 of a catheter to remove an obstruction from the lumen of a patient, where the obstruction is surrounded by a stent. The catheter is constructed of an appropriate size and of appropriate materials so that it may be inserted within and along a lumen, as is known in the art.

A common method of catheter insertion is to use a guide wire. Such a guide wire may pass at least partially through the catheter, and may be passed through a lumen by itself or through a guiding catheter. The guide wire may be first extended to a desired position in front of the catheter, and the catheter may then be advanced over the guide wire. The guide wire may pass through the entire body of the catheter, or may only pass through a section of the catheter, such as a port located near the distal end. Alternatively, the guide wire may simply be an extension from the end of the catheter, and the guide wire and the catheter may be advanced in unison. The present invention has application with any guide wire system which mechanically guides the catheter to its desired destination. It may also have an active guidance system on the same catheter, or may be used with no guidance system.

The body of the catheter is formed primarily by a catheter wall 11, that is tubular and defines a bore within the catheter. The distal end 10 of the catheter may be positioned, for example, by the use of a guide wire, where the guide wire is threaded through the lumen to the obstructed site. The catheter may then be passed over the guide wire to the site. Additional means for positioning the catheter are discussed below.

Figure 1A:
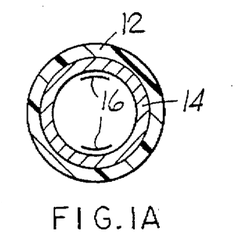
FIG. 1A is radial cross section taken along the line 1A—1A of FIG. 1.

An electrode 14 is disposed within the bore of the catheter proximate the distal end 10. The electrode 14 may be annular and may surround the interior bore of the catheter, as shown in the radial cross section view of FIG. 1A. The electrode 14 is recessed within the bore of the catheter, so that a lip 12 of the catheter wall 11 extends radially, but not distally, beyond the electrode 14.

In an electrically ablating embodiment, the catheter wall is made of an insulating material, such as any of a number of plastics. The electrode 14 is in electrical communication with a power source, such as an RF or other power source. The RF power source generates and supplies current of a suitable wave form to the electrode 14 to ablate obstructive material. The wave form may also, or in addition, be applied to enhance the bioabsorption or otherwise increase the utility of medicine or other fluids delivered through the catheter, as discussed previously and below.

Figure 4:
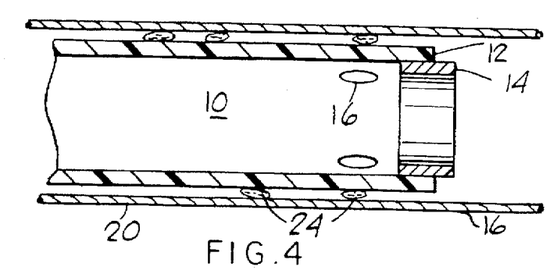
FIG. 4 is a view similar to FIG. 1B, showing the device in another position with respect to the stent.

FIG. 4 shows the distal end 10 of the catheter after it has been positioned within a lumen that has been implanted with a stent 20. The stent 20 has a tubular body that is positioned against the bore of a lumen. Stents are most commonly made of metal wire, although other materials and configurations are used, and may be used with the present invention. Obstructive material 24 is shown disposed between the stent 20 and the distal end of the catheter 10. As an example, this obstructive material may be clotted blood that has formed from the lumen wall through the openings of the stent. However, this obstruction could be any obstructive material found within any lumen, as has been described above.

The obstructive material restricts the effective diameter of the lumen implanted with the stent 20 and therefore interferes with flow of fluid (or other substance) therethrough. It is thus desirable to remove these deposits 24. This may be done by inserting the distal end 10 of the catheter through the stent 20, until the distal end has substantially passed through the stent 20. From this point, the catheter is withdrawn from the stent 20, so that its path is retraced.

Visualization means 16 may be included within the distal end 10 of the catheter, so that an operator of the device may be apprised of the exact location of the distal end 10 of the catheter in relation to the stent 20. The visualization means 16 may be ultrasound transducers that are coupled to suitable ultrasound processors, although other visualization techniques such as, for example, fiber optics, or electrical impedance sensing, may also be used. The visualization means 16 may provide information as to the amount of obstructive material, its physical configuration and location, and type of material that may be within, or outside of, the stent. The visualization means may include sensing of any other parameters of the stent, obstructive material, or lumen. The catheter operator may then precisely guide the obstruction removal process. The visualization means 16 may be used in conjunction with ablation, so that after material is ablated, visualization is again performed, the catheter is positioned to a new location, and ablation is again performed. The process may be successively repeated. The visualization means may be used, where practical, to determine the progress of the obstructive material removal, and the approaching of the outside of the lumen. For example, within a coronary artery, the thickness and composition of the plaque and approaching the intima, media, or adventitia.

The stent may also be marked with radiopaque markers and be seen using fluoroscopy techniques. Such markings, if present, may be used in conjunction with, or instead of, the visualization means 16 to determine the position of the stent 20 within the body of a patient. Conversely, the stent may be made of material which renders it highly radiopaque and makes it impossible to quantify flow or luminal opening within the framework of the stent by conventional dye injection. The imaging/visualization technique within the catheter will allow visualization in that event.

As the catheter is withdrawn, the electrode 14 will pass beneath all of the obstruction material 24 within the stent 20. When it is detected that the electrode 14 is beneath an obstructive site 24, current is applied to the electrode 14. As the electrode 14 is proximate the distal end 10 of the catheter, a path exists between the electrode 14 and the obstructive material 24 around the lip 12 of the catheter. The current travels this minimum path to the obstructive material 24, and thereby ablates the material 24.

Figure 1B:
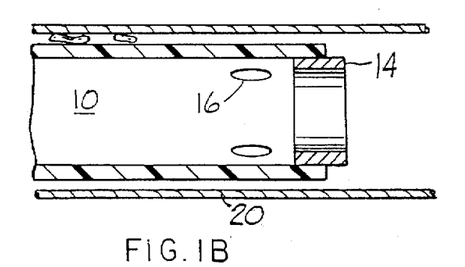
FIG. 1B is a longitudinal cross section of the embodiment of FIG. 1 within a stent.

FIG. 1B shows the catheter in a retracted position through the stent 20. As can be seen, the obstructive material distal to the distal end 10 of the catheter has been ablated. The obstructive material 24 proximal to the electrodes 14 will be ablated as the catheter is further withdrawn. When the catheter is completely withdrawn from the stent 20, virtually all of the obstructive material will have been ablated. It can be appreciated that the configuration of the electrode 14 prevents contact between the electrode 14 and the stent 20. Contact is blocked by the lip 12 of the catheter wall 11. This prevents a possible short circuit that may occur if the electrode was to contact the stent 20.

The return current from the electrode 14 to the power supply may be accomplished in several ways. A patient plate may be located on the body of the patient, and in electrical communication with the power supply. Alternatively, a bipolar embodiment could be used, as discussed below in connection with other embodiments.

It should be appreciated that while selective activation of the electrode 14 has been described as the catheter is withdrawn, any other activation method could be used. For instance, the electrode 14 could be activated as the catheter is advanced. Or, the electrode 14 could be activated when the catheter is motionless, or in any other manner, or a combination of such methods may be used. Particularly if the stent 20 is made of metal or another electrical conductor, the stent 20 may act as a virtual ground, thereby protecting the lumen in which the stent is implanted.

Figure 1C:
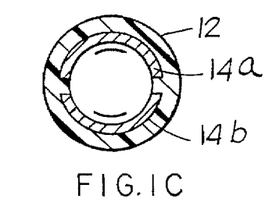
FIGS. 1C and 1D are radial cross sections similar to one FIG. 1A, depicting segmented electrodes.
Figure 1D:
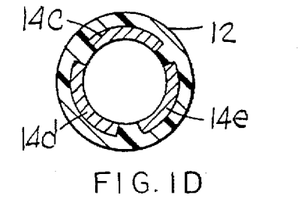

The above embodiment has been described as having a single electrode 14. However, multiple electrodes could be used instead. One configuration is to arrange electrodes around the circumference of the catheter, as shown in FIGS. 1C and 1D. In FIG. 1C, two electrodes 14a and 14b, each having a circumferential arc of approximately half the circumference of the catheter are used. Each electrode 14a and 14b could be activated individually, to selectively ablate obstructive material proximate the electrodes. FIG. 1D shows a catheter with three electrodes 14c, 14d, and 14e arranged around the circumference of the catheter. This allows for greater resolution of ablation for non-symmetric obstructions. Of course, more than three divisions may be used, allowing for still greater resolution. The use of multiple electrodes is discussed in greater detail in the context of alternative embodiments of the invention, below.

While the above embodiment has been described as using electrosurgical ablation, it should be appreciated that other forms of ablation may be similarly used. For instance, the ablation may occur as the result of standard electrosurgical wave forms of cutting or coagulation, customized wave forms, dc current, pulsed current, modulated current using any combination of modulating and carrier wave forms, laser energy of any frequency and modulation, direct mechanical energy, acoustical or ultrasonic energy, direct application of thermal energy, or corrosive chemicals.

Figure 2:
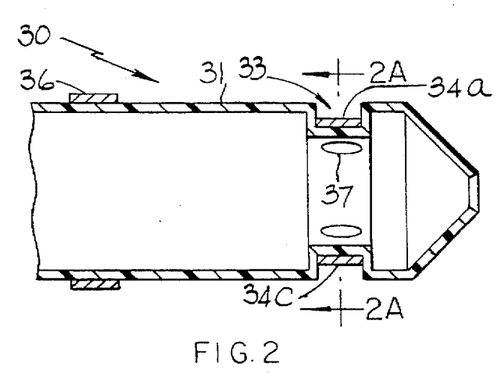
FIG. 2 is a longitudinal cross section of the distal end of an alternate embodiment of the invention, including an electrode recessed within a ridge.
Figure 2A:
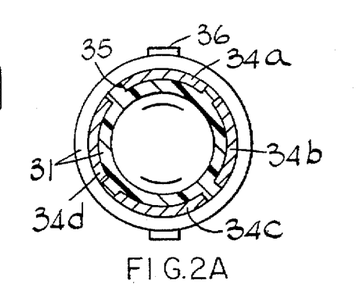
FIG. 2A is a radial cross section taken along the line 2A—2A of FIG. 2.

Referring to FIG. 2, an alternate embodiment of a distal end 30 of a catheter is shown in longitudinal cross section. The distal end 30 is formed by a catheter wall 31. The distal end 30 is preferably tapered, so that the catheter may be smoothly advanced through a lumen. A recessed annular ridge 33 defines a groove in which electrodes 34a, 34b, 34c, and 34d are seated. As shown in the radial cross section of FIG. 2B, the electrodes 34 substantially surround the surface of the distal end 30, but are separated by thin strips of the catheter wall 35, so that they are electrically isolated from one another. The electrodes 34 are sized so that they are recessed within the annular ridge 33. A return electrode 36 is located on the catheter proximal to the electrodes 34. The electrode 36 may surround the catheter wall 31, or may have any other shape. The electrode 36 has a relatively large surface area compared to the surface area of each of the electrodes 34, so that the current density through the electrode 36 is low enough to prevent damage to tissue adjacent to the electrode 36.

Figure 5:
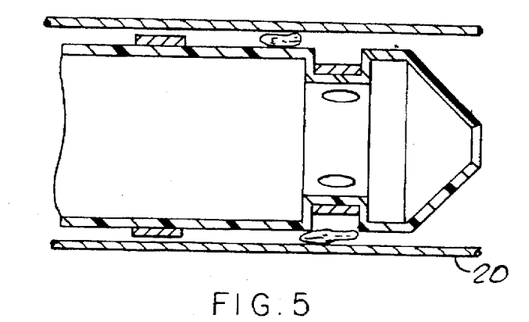
FIG. 5 is a longitudinal cross section similar to FIG. 2, showing the device within a stent.

FIG. 5 shows the catheter of FIG. 2 within a stent 20 implanted within a lumen. The catheter may be positioned in the stent by the use of the visualization means 37. As discussed above, these visualization means may include ultrasound transducers, fiber optics, or any other visualization means.

Figure 2B:
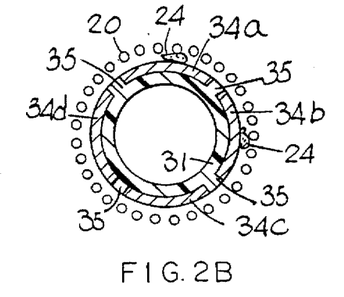
FIG. 2B is the radial cross section of FIG. 2, showing the distal end of the device within a stent.

The catheter may be withdrawn or advanced through the stent, and any of the electrodes 34 may be activated when the electrode passes obstructive material 24. The circumferential division of electrodes 34a, 34b, 34c, and 34d allows for greater selectivity of obstruction ablation. Obstructions may or may not be located symmetrically around the circumference of a lumen or a stent. Therefore, it may be desirable to apply ablation selectively around the circumference of the catheter. Referring to FIG. 2B, the catheter of FIG. 2 is shown within a stent 20 with electrodes 34a and 34b adjacent obstructive material 24, and electrodes 34c and 34d not adjacent obstructive material. In that case, electrodes 34a and 34b may be activated, and electrodes 34c and electrodes 34d may be made inactive. Of course, suitable electric switching apparatus must be included in the circuit linking electrodes 34 and the power supply generator, as is well known in the art of electronics.

In this example, current will flow from the electrodes 34a and 34b, through the obstructive material 24, and to the return electrode 36. The obstructive material 24 will be ablated in this process. It should be appreciated that the current flow may be directed in a number of variations. The current flow may be from an active electrode, through the stent, and to the return electrode or electrode(s). The current flow may also be directed so as to keep more or less of the current flow within the framework of the stent. While the above embodiment has been described with a return electrode, ablation could be performed without a specific return electrode, so that the current returns to the power supply through capacitive coupling, or through an electrode attached to the patient's skin.

The return electrode 36 may be sized so that it will contact the stent 20, thereby grounding the stent. This will lower the impedance between the return electrode 36 and the electrodes 34, and allow for precise ablating of obstructing material between the electrodes 34 and the stent 20. However, it may be inconvenient to have the electrode 36 sized to contact the stent 20, because the electrode may then interfere with the longitudinal motion of the catheter through the stent 20. One solution to this problem is to use an inflatable balloon located beneath the electrode 36 to selectively increase the diameter of the catheter at the position of the electrode 36. The balloon may be deflated when the catheter is moved through the lumen, and may be inflated when the movement of the catheter is halted and current is applied through the electrodes 34.

Good results may be also be obtained without placing the electrode 35 in direct electrical communication with the stent 20. Further, if a metallic stent 20 is used, electricity will flow through the stent 20, instead of the surrounding tissue, because of the superior conductance of metal, thus causing the stent to act as a virtual ground.

The division of the electrodes 34 into four units is shown as an example only, it being understood that either more or fewer divisions could be used. A non-segmented, unitary electrode could be used as described in the embodiment shown in FIG. 1, although this would not allow for circumferentially selective ablating. More than four segments would allow for more circumferential selectivity, although, after a point, such selectivity may be unnecessary. The precise number of divisions is a matter of design choice and may depend on the specific application.

Figure 3:
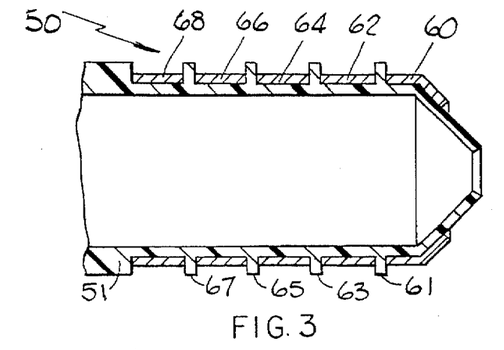
FIG. 3 is a longitudinal cross section of the distal end of another embodiment of the invention, showing a plurality of axially spaced electrodes.

Another embodiment of the distal end 50 of a catheter according to the present invention is shown in longitudinal cross section in FIG. 3. A catheter wall 51 defines the body of the catheter. A series of five electrode rings 60, 62, 64, 66, and 68 are disposed around the distal end 50. Five rings are shown and described only as an example; any number or rings may be used with good results depending on the specific application. Each ring may be either a solid ring and thus form a unitary electrode, or may be segmented into separate electrodes as described above. The use of segments allows for circumferentially selective ablation. Each ring (and ring segment, if a segmented ring is used) may be individually activated by being placed in electrical communication with the power supply. The catheter wall 51 includes spacers 61, 63, 65, and 67 that project axially away from the catheter axis. The spacers are situated between electrode rings, and have a diameter greater than the rings, so that the electrodes are prevented from contacting rigid objects external to the catheter.

Figure 6:
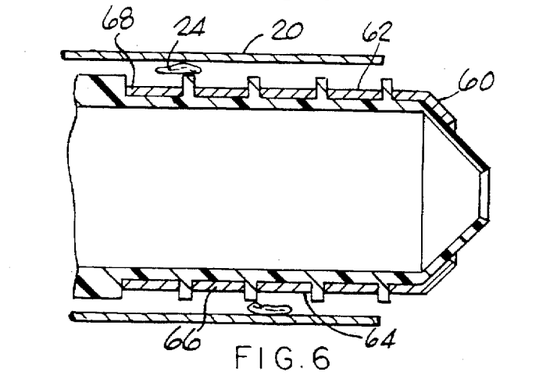
FIG. 6 is a longitudinal cross section similar to FIG. 3, showing the device within a stent.

In one embodiment of the invention, each of the rings 60, 62, 64, 66, or 68 may be used as either an active or a return electrode. Thus, any combination of the electrodes may be selected as active electrodes, and any combination of electrodes may be selected as return electrodes. FIG. 6 shows the distal end 50 of the catheter situated in a stent 20, including obstructive material 24. Preferably, the section of the distal end 50 including electrodes 60, 62, 64, 66, and 68 is longer than the stent 20. Good results may be obtained if the active electrode area is approximately the same length as the stent 20, or a considerably longer distal end 50 may be used, such as one with a length in the range of, for example, about two to ten times the length of the stent 20.

The catheter preferably includes means to sense the impedance, including the resistance, capacitance, and inductance, between a selected active electrode and a selected return electrode. Such impedance detectors are well known in the art of electronics and may take a variety of forms, generally sensing the amount of power required to produce a given current flow between two electrodes, as well as other parameters. Impedance sensing allows for the determination of the position of the distal end 50 with respect to a metallic stent 20.

To position the catheter, an electrical signal may be sent to one of the electrodes, such as the middle electrode 64. This signal is preferably of a significantly lower magnitude, and may have other electrical parameters, than the ablating current that may be transmitted through an electrode when ablation is desired. The other electrodes 60, 62, 66, and 68 will be sequentially selected as the return electrodes. The impedance sensed between the electrode 64 and the selected return electrode will vary depending on the position of the distal end 50; if both the electrode 64 and the selected return electrode are enclosed within the stent 20, the impedance between the electrodes will be much lower than if either both of the electrodes are not within the stent or if only one electrode is within the stent. This is because a metallic stent 20 is a better conductor than the ordinary fluids and tissue found within the body of a patient, so that impedance will be lower when the signal travels through the stent 20 rather than simply through the body.

In the context of FIG. 6, a relatively high impedance will be found between electrode 64 and electrode 60, because electrode 60 is not within the stent. A relatively low impedance will be found between electrode 64 and electrode 62, because electrodes 62 and 64 are within the stent. Likewise, the impedance will be relatively low between electrodes 64 and 66, and will be relatively high between electrodes 64 and 68. The values of what impedance values are relatively low and what are relatively high will depend to some extent on the specific catheter design and the stent configuration. The catheter may be calibrated through routine experimentation so representative values of the impedance between a specific set of electrodes for a given position in relation to a stent may be obtained.

After performing the above impedance sensing, it will be known that electrodes 64, 66, and 62 are within the stent and that electrodes 60 and 68 are not within the stent. Ablation may then be performed, directing the current between electrodes 62, 64, and 66. Electrodes 60 and 68 will remain electrically inactive and will not take part in the ablation.

It may happen that none of the electrodes are within the stent 20. In that event, a relatively high impedance will be found between all of the electrodes. The distal end 50 of the catheter may then be repositioned, and impedance sensing being again performed. Successive iterations of impedance selection and distal end 50 movement may be performed until the distal end is within the stent 20. The desired position is that the stent 20 be completely filled by the distal end 50, so that there is no section of the stent 20 that does not contain an electrode.

In the above described embodiment, the stent 20 is not grounded. However, as explained above in connection with the impedance sensing, the stent may conduct current and therefore act as a virtual ground, shielding all tissue located exterior to the stent. Therefore, higher currents may be used while reducing the risk of damaging the lumen wall in which the stent is located. These currents will ablate the obstructive material 24 located within the stent. However, the current may be contained within the stent by use of appropriate energy, if desired.

Figure 8:
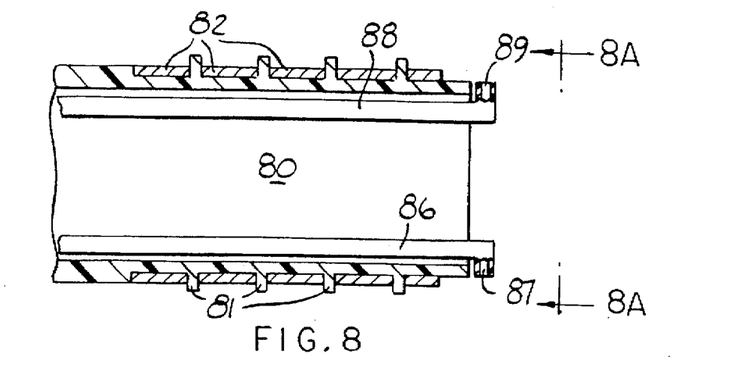
FIG. 8 is a longitudinal cross section of an embodiment of the invention similar to that depicted in FIG. 3, without a longitudinally active electrode, and including therapeutic enhances.

It should be appreciated that the distal end 50 used within the catheter is exemplary only, and that many modifications could be made, such as in the number and configuration of electrodes. For instance, the catheter of FIG. 3. is shown with the most distal ring 60 being tapered along with the extreme distal end 50 of the catheter. This allows for "forward" ablation, i.e., ablation longitudinal to the axis of the catheter. However, a modified distal end 80 as depicted in FIG. 8 shows a series of electrode rings 82 without a forward facing distal electrode ring. Instead, the most distal of the rings 82 surrounds the catheter and does not have a distally projecting component. Spacers 81 insure that the electrode rings 80 are separated from the stent.

Also, the impedance sensing may be performed otherwise than explicitly explained above. For instance, it is not necessary to use the middle electrode in impedance sensing—any set of electrodes may be used. As another example, one electrode could be selected as active electrode and the remainder of electrodes could be simultaneously selected as a return electrode, allowing for simultaneous impedance sensing and location determination.

Figure 7:
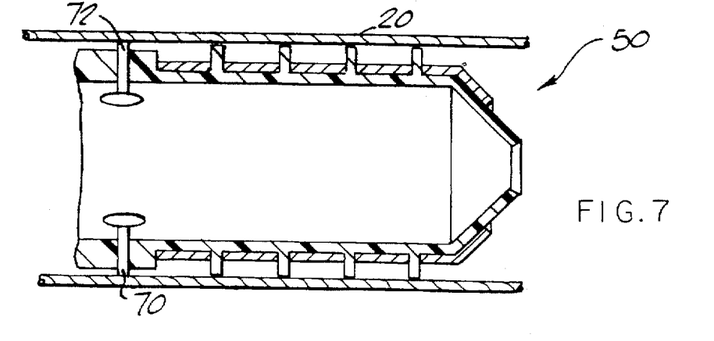
FIG. 7 shows an embodiment of the invention similar to FIG. 6, with the stent being grounded.

It may be desirable to modify the above embodiment to directly ground the stent. While the stent acts as a virtual ground in the above example, a direct electrical connection will improve the shielding effect of the stent. One method of grounding the stent is through the use of conducting connecting stylets or probes 70 and 72, as shown in FIG. 7. The stylets or probes 70 and 72 are at their proximal ends placed in electrical communication with the power supply. The distal ends of the stylet or probes protrude from the body of the catheter until electrical contact is made with the stent 20, as shown in FIG. 7, thereby grounding the stent 20. The positioning of the stylets or probes 70 and 72 may be performed by any means to position wires within a lumen, such being routinely performed in, for example, the insertion of guide wires into a lumen. The stylets or probes 70 and 72 may be maintained within the catheter until the distal end 50 is correctly positioned, so that they will not interfere with the motion of the catheter through the lumen. After the catheter is positioned and the stylets or probes 70 and 72 are attached and ablation is performed, the stylets or probes may be retracted into the catheter and the catheter may be removed from the lumen. Non-retractable stylets or probes may also be used.

Figure 10A:
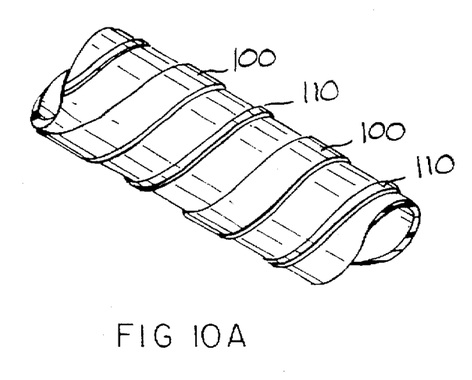
FIGS. 10A and 10B show separate embodiments of the distal end of a catheter with separate ablating and sensing electrodes.
Figure 10B:
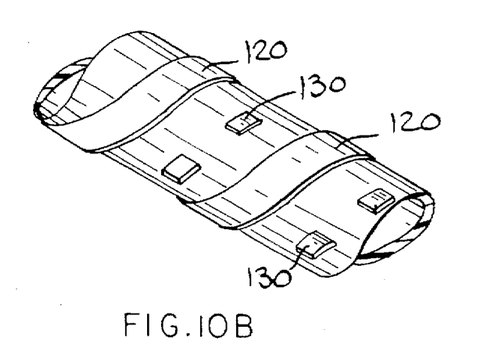

In the above embodiment, sensing the electrical parameters as modified by the presence of the stent has been described using the same electrodes that may also be used to perform ablation. However, different electrodes could be used to perform sensing than perform ablation. FIG. 10A shows a section of a catheter distal end with a series of ablating electrodes 100 and a separate series of sensing electrodes 110. The sensing electrodes may, but need not be, smaller than the ablating electrodes, as in general the sensing electrodes will supply less energy than the ablating electrodes. FIG. 10B depicts an alternate embodiment of a catheter with separate ablating electrodes 120 and sensing electrodes 130. The sensing electrodes need not be annular; they may be window-like recessions or have any other form. The ablating electrodes may also have any configuration as discussed above.

Figure 9:
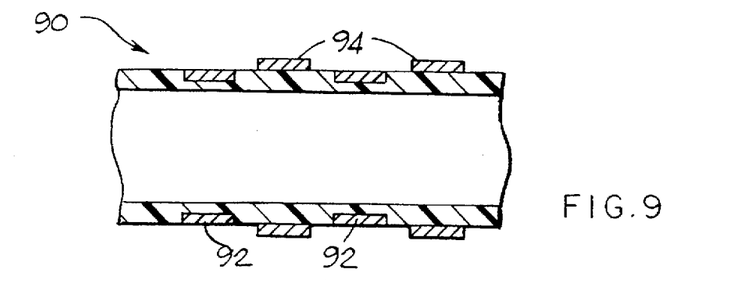
FIG. 9 is a longitudinal cross section of an embodiment of the invention with active electrodes of two different radial extensions.

Any of the above described catheters or variations thereof may be further modified by the addition of electrodes that may be effectively used to ablate obstructive material in a lumen that is not contained within a stent. An example of such a catheter is shown in FIG. 9, depicting the distal end 90 of the catheter. The distal end includes two electrode rings 94 that are radially spaced away from the body of the catheter, and two electrode rings 92 that do not radially extend as far as the electrode rings 94. The electrode rings 92 will thus be shielded from a stent in which the distal end 90 of the catheter is placed, by the protrusion of the electrode rings 94. While in a stent, the electrode rings 94 act as spacers similar to the spacers 61, 63, 65, and 67 shown in the embodiment depicted in FIG. 3. When the distal end 90 is positioned within the stent, the electrodes 92 may be activated to ablate any obstructive material within the stent.

When the distal end is not positioned within a stent, the electrodes 94 may be positioned directly against obstructive material and activated so as to ablate the material. When a stent is not involved, it is generally desirable to maintain actual contact or near contact between an ablating electrode and obstructive material. The electrodes may be activated as the catheter is projected through a lumen, or withdrawn, or when the catheter is held steady.

The electrode rings shown in FIG. 9 may be solid rings or may be segmented in any manner, as discussed above. Further, it should be understood that the number and configuration of electrodes in FIG. 9 is only to illustrate the concept of using separate electrodes within and without a stent. Any number of rings could be used, in any configuration. Separate spacers instead of electrodes could be used. Or, recessed electrodes could be used instead of spacers, as described in an above embodiment. The electrodes to be used within a stent may be positioned on a separate section of the catheter instead of being commingled with the electrodes to be used out of the stent.

Figure 11A:
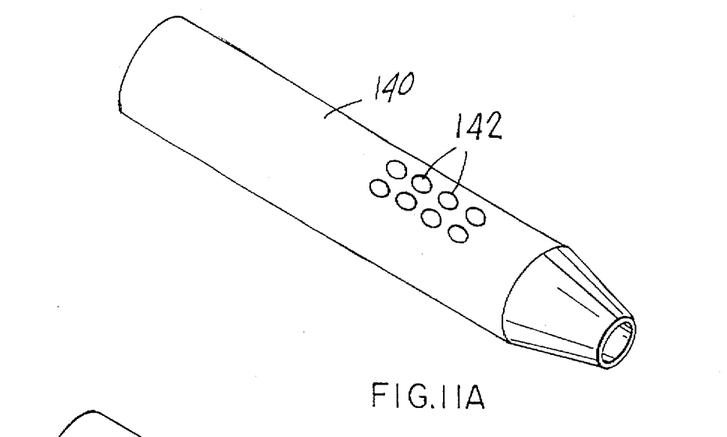
FIGS. 11A, 11B, and 11C show perspective views of separate embodiments of the distal end of a catheter with a mechanical insulator to prevent contact between the electrode and stent.
Figure 11B:
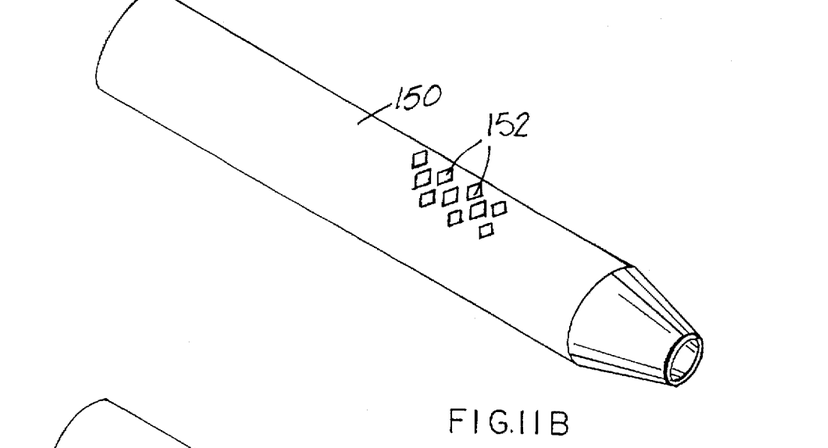
Figure 11C:
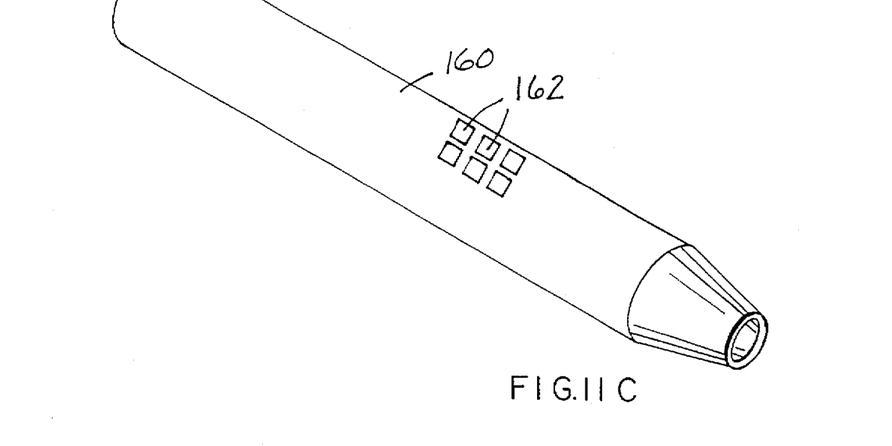

Other catheter configurations may be used to separate the electrode(s) from physically contacting the stent. FIGs. 11A, 11B, and 11C show perspective views of three different insulation patterns where insulation covers an electrode. In FIG. 11A, approximately spherical holes in an insulation sheath 140 prevent physical contact between an electrode 142 and a stent. In FIG. 11B, cross hatching in the insulation sheath 150 shields and electrode 152. In FIG. 11C approximately rectangular holes in an insulation sheath 160 shield an electrode 162. The number and dimensions of the holes or cross hatches is determined by the minimum exposed area necessary for ablation, and the maximum insulated area required to insure non-contact with the stent frame. The mechanical insulator may be of any design or shape, or suitable material; the patterns of FIGS. 11A, 11B, and 11C are merely representative patterns. The substrate used in the fabrication of the insulation may be the same as the catheter tubing. However, any substrate having suitable mechanical and electrical properties may be used. The insulation may be used with any number of electrodes, of any shape and configuration.

Figure 12:
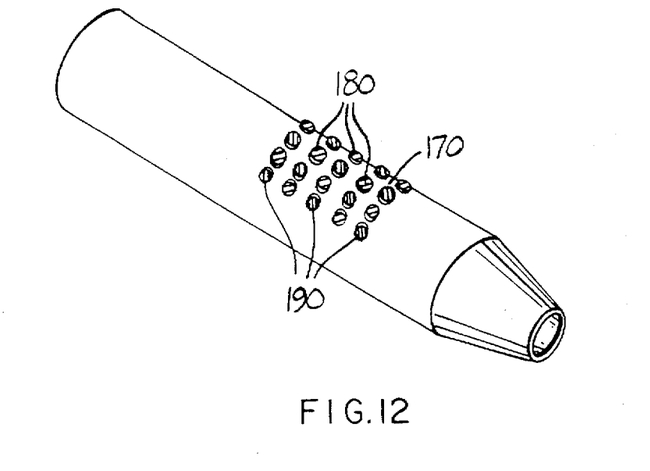
FIGS. 12 and 12A show an electrode arrangement and schematic respectively of embodiment of the invention using an array of interleaved active and return electrodes.
Figure 12A:
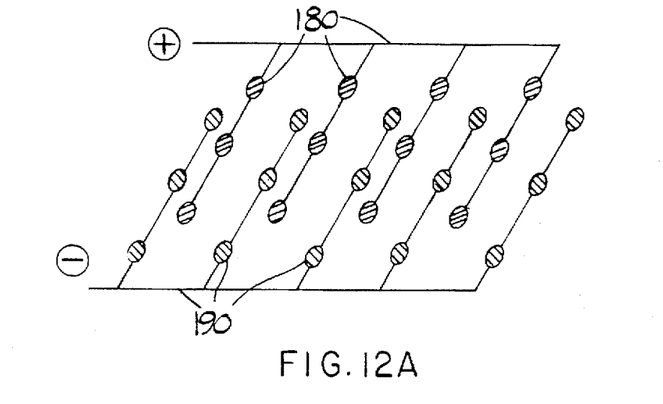

With reference to FIGS. 12 and 12A, a further electrode arrangement is provided that allows for another method of varying the electric field and current density supplied by the electrodes. The arrangement further provides for increased flexibility of the portion of the catheter that supports the electrodes. As shown in FIG. 12, the distal end of a catheter may include perforated insulation 170 similar to that described in connection with FIG. 11. The insulation depicted in FIG. 12 is similar to that of FIG. 11A as an example only—other insulation could be used with good results. The insulation 170 perforations expose an electrode array having interspaced positive (or signal) electrodes 180 and negative (or return) electrodes 190. The positive electrodes 180 are arranged in parallel, as are the negative electrodes 190. The electrodes are arranged so that the positive electrodes 180 are spaced about the catheter in a plurality of rings. The negative electrodes 190 are similarly spaced about the catheter. Each positive ring may be substantially coincident with each negative ring. However, the actual position of the positive and negative electrodes are tangentially offset so that no surface area of the catheter has both positive and negative electrodes. The physical interrelationship of the positive and return electrodes allows for increased control of the electric field, compared to an arrangement that does not have interleaved positive and negative electrodes.

The use of a plurality of smaller electrodes allows for greater flexibility of the catheter head, because the catheter body is in general more flexible than the electrodes. The use of numerous, separated electrodes allows the catheter body to flex in between the electrodes. A solid electrode that surrounds the catheter body, or a major portion of the catheter body, in contrast, prevents the catheter from flexing. A less flexible catheter may interfere with the physical insertion of the catheter through a lumen or stent.

The parallel electrical circuitry is depicted in FIG. 12A. FIG. 12A depicts a representative portion of positive electrodes 180 and negative electrodes 190, not the entirety of the electrodes. As can be seen, the positive electrodes 180, separate positive electrode "rings" 180 are connected in parallel with one another, as are separate negative electrode 190 "rings", with the positive and negative electrodes intermeshed with each other.

Another aspect of the invention is the ability to supply fluids through the catheter and introduce these fluids into the lumen in which the catheter has been inserted. With reference to FIG. 8, the catheter includes fluid ducts 86 and 88 which extend to the distal end of the catheter. Fluid ports 87 and 89 allow fluid to be introduced into the lumen from the fluid ducts 86, 88 respectively. Such fluid is typically medicine to enhance the ablating, therapeutic, or diagnostic process in conjunction with the electrode ablation. The fluid may be deposited, or even forced, from the ducts 87 and 89 into the surrounding tissue. Along with the fluid deposition, the catheter may include means to enhance the effect of the fluid on the surrounding tissue. Such means may include, but are not limited to, the application of electrical energy, such as by the electrodes 82; any other electromagnetic energy such as light; mechanical energy such as direct stimulation; ultrasound or acoustic or other vibrational energy. Such means may be applied prior, during, or subsequent to the application of fluid, or in any combination of these time periods. Such means, in addition to the electrodes 82, may be conveyed through the body of the lumen, as shown in cross section in FIG. 8A.

Figure 8A:
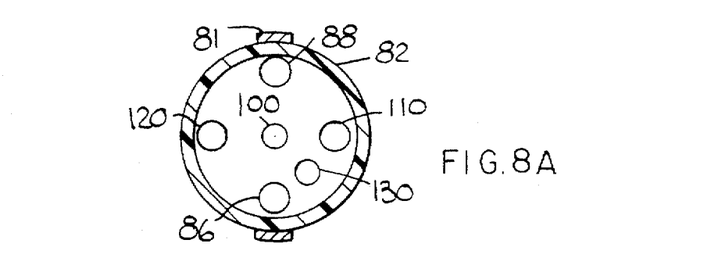
FIG. 8A is radial cross section of FIG. 8.

A guide wire 100 may be used to position the catheter to the desired site, along with any desired visualization means as described above. The fluid is delivered through ducts 86 and 88. Ducts 110 and 120 may deliver therapeutic energy, as discussed above, to be used in conjunction with the fluid. The fluid delivery system with therapeutic energy may be used in conjunction with any of the described embodiments, or any variations thereof. Also, the fluid system is not limited to two ducts—one duct or any number of ducts may be used to deliver as many types of fluid as is desired. The fluid need not be liquid; it may be gaseous or in any other form. In addition, a suction duct 130 may be used to remove substances from the lumen, such as therapeutic fluid, obstructive material, or any other substance. Also, while two fluid ports have been described, any number of fluid ports, including one or more, could be used.

The invention claimed is:

1. A device for ablation of obstructive material within a stent, the device comprising:
    an elongate flexible tube having a distal end and a proximal end and an interior surface therebetween, the tube defining an axial direction along a length of the tube and a radial direction radially away from the tube;
    a first ablation electrode positioned within said interior surface proximate the distal end;
    an ablation power supply in electrical communication with said ablation electrode;
    wherein said first ablation electrode is shielded from physical contact with the stent by said tube when the first ablation electrode is positioned within the stent; and wherein said first ablation electrode is positioned so that it is electrically unobstructed in the radial direction by the tube while being shielded from physical contact with the stent, thereby being electrically operative in the radial direction with respect to its position along the axial direction.

2. The device of claim 1, wherein said first electrode is located on the interior surface of said elongate flexible tube, and said elongate tube has a lip extending distal to said first electrode.

3. The device of claim 2, further comprising a first plurality of electrodes on the interior of said elongate flexible tube proximate the distal end, said electrodes being circumferentially spaced about the interior of the tube; and the power supply allowing current to be selectively supplied to any of the plurality of electrodes.

4. The device of claim 3, further comprising a return electrode in electrical communication with the current supply, the return electrode being attachable to a patient.

5. The device of claim 3, further comprising means for visualizing the location of said distal end of said elongate tube and determining the composition and amount of the obstructive material.

6. The device of claim 5, wherein the means for visualizing include an ultrasound transducer.

7. The device of claim 5, wherein the means for visualizing include fiber optics.

8. The device of claim 5, wherein the means for visualizing include a fluoroscopic device.

9. The device of claim 1, wherein said tube has a groove proximate said distal end, said groove being formed within an exterior surface of said tube; said first electrode being situated within said groove; and said first electrode being sized so that it is recessed within the groove, whereby said electrode is unobstructed in the radial direction.

10. The device of claim 9, further comprising a return electrode located on said tube.

11. The device of claim 10, wherein said return electrode may be positioned so as to physically contact said stent.

12. The device of claim 1, further comprising a plurality of grooves within said tube, each of said grooves being formed within an exterior surface of said tube, and a plurality of electrodes, wherein at least one of said plurality of electrodes is recessed within each of said plurality of grooves, and whereby said electrodes are unobstructed in the radial direction.

13. The device of claim 1, further comprising a plurality of electrodes located on said tube, at least some of the plurality of electrodes being located further distal on the catheter than other of the plurality of electrodes; and the power supply allowing each of the plurality of electrodes to independently receive current.

14. The device of claim 13, wherein at least one of the plurality of electrodes may be alternately made a supply or return electrode by the current source.

15. The device of claim 13, further comprising means for sensing the impedance between at least two of said electrodes, the impedance sensing means detecting whether one or both of the at least two electrodes are within the stent so that only an electrode within the stent is suppled with ablative current.

16. The device of claim 15, further comprising spacers disposed about said tube proximate said electrodes, said spacers projecting radially further from the tube than said electrodes, said spacers projecting a distance sufficient to prevent said electrodes from contacting the stent.

17. The device of claim 16, wherein said plurality of electrodes are arranged in a series of rings located around said tube.

18. The device of claim 1 wherein the electrode directs current distal to the distal end of the device.

19. The device of claim 1, further comprising a second electrode, the second electrode projecting radially further from the axis of tube than the first electrode.

20. The device of claim 19, further comprising a first plurality of electrodes and a second plurality of electrodes; each of the first plurality of electrodes being shielded from contact with the stent when each of the first plurality of electrodes are positioned within the stent; and each of the second plurality of electrodes extending further from the tube axis than each of the first plurality of electrodes.

21. The device of claim 1, further comprising means for delivering bioactive fluid exterior to the tube.

22. The device of claim 21, further comprising means for delivering energy to increase the bioactivity of the fluid.

23. The device of claim 22, wherein the energy to increase the bioactivity of the fluid consists of electrical energy, optical energy, mechanical energy, or acoustical energy.

24. The device of claim 1, further comprising at least two sensing electrodes proximate the distal end, and means to sense the impedance between the sensing electrodes.

25. The device of claim of claim 1, further comprising insulating material that partially covers the electrode, said insulating material separating the electrode from the stent.

26. The device of claim 25, wherein the insulating material is perforated.

27. The device of claim 25, wherein the insulating material is cross hatched.

28. The device of claim 1, further comprising:
a first plurality of electrodes including the first electrode, the first plurality of electrodes being disposed about the distal end of the catheter;
a second plurality of electrodes, each of the second plurality of electrodes being disposed about the distal end of the catheter;
the first plurality of electrodes being interspaced with the second plurality so that members of the first plurality alternate with members of the second plurality across a portion of the distal end of the catheter; and
wherein the first plurality are electrically interconnected in parallel to a first polarity and the second plurality are electrically interconnected in parallel to an opposite polarity.

29. The device of 28, wherein the first plurality of electrodes and the second plurality of electrodes are arranged in a series of spaced rings.

30. A method of removing obstructive material from the interior of an axially extending stent implanted in a subject, comprising:
engaging said subject with an elongate electrosurgical device including a tube having a proximal end and a distal end and an interior surface therebetween, said device having an ablation electrode proximate said distal end, said ablation electrode being positioned within said interior surface such that it is prevented from contacting the stent by said tube and is electrically unobstructed in a radial direction in relation to an axial direction defined by said stent while being shielded from physical contact with the stent;
positioning said device so that the ablation electrode is at least partially with the stent; and
supplying current from a current source to said ablation electrode to ablate said obstructive material.

31. The method of claim 30, wherein the positioning step includes using visualization means to visualize the position of the distal end in relation to said stent.

32. The method of claim 30, wherein the visualization means include ultrasound transducers.

33. The method of claim 30, wherein the visualization means include fiber optics.

34. The method of claim 30, wherein said device contains at least two electrodes proximate said distal end, and the positioning step includes determining the position of the distal end in relation to the stent by establishing current flow between at least two of said electrodes and determining the impedance therebetween.

35. The method of claim 34, further comprising the step of establishing direct electrical communication between said stent and said current source.

36. The method of claim 30, further comprising the step of supplying bioactive fluid through the device to medicate said subject.

37. The method of claim 36, further comprising supplying energy to increase the bioactivity of the fluid.

38. The method of claim 37, wherein the energy to increase the bioactivity of the fluid consists of electrical energy, optical energy, mechanical energy, or acoustical energy.

39. The method of claim 30 further comprising the step of ablating material exterior to said stent, the step of ablating material exterior to said stent being performed by a second electrode.

40. The method of claim 30, wherein the positioning step includes measuring the impedance between at least two sensing electrodes located on said device.

41. A therapeutic method to increase flow through an at least partially obstructed lumen, comprising the steps of:
deploying a stent with the abstract lumen;
inserting an ablation device within the stent, the device having
(a) an elongate flexible tube having a distal end and a proximal end and an interior surface therebetween, the tube defining an axial direction along a length of the tube and a radial direction radially away from the tube;
(b) a first ablation electrode positioned within said interior surface proximate the distal end;
(c) an ablation power supply in electrical communication with said ablation electrode;

(d) wherein said first ablation electrode is shielded from physical contact with the stent by said tube when the first ablation electrode is positioned within the stent; and wherein said first ablation electrode is positioned so that it is electrically unobstructed in the radial direction by the tube while being shielded from physical contact with the stent, thereby being electrically operative in the radial direction with respect to its position along the axial direction; and using said ablation device to ablate obstructions from the stent.

* * * * *